United States Patent [19]

O'Brien

[11] Patent Number: 4,921,790
[45] Date of Patent: May 1, 1990

[54] TUMOR SPECIFIC ASSAY FOR CA125 OVARIAN CANCER ANTIGEN

[75] Inventor: Timothy J. O'Brien, Little Rock, Ark.

[73] Assignee: Research Corporation, New York, N.Y.

[21] Appl. No.: 42,498

[22] Filed: Apr. 24, 1987

[51] Int. Cl.$^5$ .................. G01N 33/53; G01N 33/543; C07K 15/14; C12N 1/00

[52] U.S. Cl. ..................................... 435/7; 435/172.2; 435/174; 435/810; 436/501; 436/518; 436/548; 436/808; 436/813; 530/350; 530/387; 530/808; 530/810; 935/108; 935/110

[58] Field of Search ............. 435/7, 68, 172.2, 240.27, 435/810, 174, 176, 177; 436/501, 518, 540, 548, 808, 813, 800, 804; 530/387, 808, 828, 853, 350, 413, 810; 935/106, 108, 110

[56] References Cited

U.S. PATENT DOCUMENTS

| | | | |
|---|---|---|---|
| 4,584,278 | 4/1986 | Knauf . | |
| 4,623,621 | 11/1986 | Pestka | 436/548 |
| 4,666,845 | 5/1987 | Mattes et al. | 436/548 |
| 4,713,351 | 12/1987 | Knauf | 436/548 |

FOREIGN PATENT DOCUMENTS 8500663  2/1985  PCT Int'l Appl. .................... 435/7

OTHER PUBLICATIONS

Masuno et al., Cancer Research, vol. 44, Mar. 30, 1984, pp. 2813-2819.
Bast et al., The New England Journal of Medicine, vol. 309, No. 15, 1983, pp. 883-887.
Knauf and Urback, "A Study of Ovarian Cancer Patients using a Radioimmunoassay for Human Ovarian Tumor-Associated Antigen OCA," *Am. J. Obstet. Gynecol., 138:* 1222, 1980.

*Primary Examiner*—David M. Naff
*Assistant Examiner*—Florina B. Hoffer
*Attorney, Agent, or Firm*—Scully, Scott Murphy & Presser

[57] ABSTRACT

The present invention relates to a 40 kilodalton subunit of serous cystadinocarcinoma ovarian tumor associated antigen CA125, useful in the diagnosis and monitoring of ovarian cancer. It also relates to an immunoassay method for detection of the antigen in serum for diagnosis and monitoring purposes.

9 Claims, No Drawings

TUMOR SPECIFIC ASSAY FOR CA125 OVARIAN CANCER ANTIGEN

GOVERNMENT SUPPORT

The present invention was supported in part by the National Institute of Health, Grant No. 40406.

FIELD OF THE INVENTION

The present invention relates to a novel subunit of an ovarian tumor-associated antigen useful in detection of ovarian cancer. It also relates to a method of diagnosis and monitoring of ovarian tumors utilizing the novel subunit as an indicator.

BACKGROUND OF THE INVENTION

The effective detection and diagnosis of cancer at an early stage in its development may be critical in the ultimate successful treatment of the disease. It is further extremely important that the diagnosis accurately pinpoint the type or location of the tumor since different tumor types may frequently require the use of different chemotherapeutic or treatment regimens. Finally, it is also necessary that the testing procedure used in diagnosis be precise to such an extent that there is minimal danger that either false positives or false negatives will produce an inaccurate diagnosis.

In this connection, the various procedures coming under the heading of "immunoassay" have shown particular promise in development of tumor specific diagnostic testing. Immunoassay relies, in principle, on the natural reactions of the body's immune system to the presence of foreign substances introduced into the body. The immune system is provoked by these foreign materials, for example, infectious organisms such as bacteria or viruses, to produce antibodies which react specifically with the foreign substance (or antigen) and which, if effective, aid in the elimination of the organisms or foreign matter from the body. The production of antibodies, of course, is not limited to the presence of infectious microorganisms but is also observed in response to many materials which are not normally found in circulation in the body such as cancerous cells, foreign blood group antigens, or fetus-specific antigen.

The relative specificity of antibody for a particular antigen has provided the basis for highly specific and accurate diagnostic testing for various physiological conditions such as infectious diseases, specific tumors, pregnancy and presence of drugs in the body. In practice, the test operates by exposing a test sample suspected of containing a specific antigen associated with a particular disease condition, or antibodies to a particular microorganism, such as the AIDS virus, to a detectably labelled corresponding "immunological partner," i.e., the corresponding antibody or antigen. Alternately, in a "sandwich" type of assay, a test sample containing the antigen to be detected is added to a corresponding antibody, and this is followed by addition of a second labelled antibody to the antigen, providing a detectably labelled "sandwich," indicating the antigen's presence. Competitive binding assays also exist, in which the relative amount of binding of an antigen mimic to an antigen-specific antibody in the test sample is used to indicate the relative amount of antigen present in the sample. In all these immunoassays, a reaction between antigen and antibody indicates the presence of the suspected condition, the reaction being made visibly detectable by the presence of a label on the antigen or antibody. The most frequently used labels are enzymes, to which a substrate is added, causing a catalytic reaction producing a color change; also commonly used are fluorescent, chemiluminescent or radioactive molecules. A wide range of variations on immunoassay techniques are currently available as can be seen, for example, by reference to U.S. Pat. Nos. 4,016,043; 4,424,279 and 4,018,653.

The successful development of an accurate immunoassay for disease detection, of course, requires that an appropriate antigen or antibody is available with which to conduct the assay. For example, the ideal antigen is one which is highly specific to the particular condition of interest, the identification of which, in the test sample, will definitively show the presence of the causative agent or other associated factor. Such antigens would include, for example, a lipopolysaccharide peculiar to a particular species of bacterium; a glycoprotein only found in the coat of a specific type of virus; or cell surface antigens only found in abnormal cell types such as tumor cells. The selection of the appropriate antigen is critical to the accuracy of any diagnosis since selection of an antigen which is not specific to a particular cell type or species may result in a large number of false positive reactions by identification of unrelated cells or organisms also carrying the antigen.

A particular effort has been made to identify tumor cell antigens as markers for specific types of tumors. Developments of a test which can identify a disease connected antigen with specificity will be of substantial value to the clinician not only in early diagnosis, but also in evaluating the progression of the disease and determining effectiveness of ongoing therapy. Some success has been achieved in the development of immunoassays for tumor specific antigens. For example, human chorionogonadotropin (hCG) has been effectively applied to the monitoring of trophoblastic disease. Similarly, certain other antigens, such as alphafetoprotein (AFP), prostatic acid phosphatase (PAP) and carcinoembryonic antigen (CEA), have all been effectively been employed in detection and monitoring of tumors in general and in particular connection with testicular, prostate and colorectal carcinomas. However, outside the aforementioned collection of substances, there has been a relative dearth of other antigens which are truly useful in accurate diagnosis and monitoring; this has been proven particularly true with respect to gynecologic malignancies, especially ovarian carcinomas, which have frequently already spread throughout the pelvic cavity before diagnosis of the condition. Many of these carcinomas typically exhibit a very agressive growth pattern and generally respond well to chemotherapy. Thus, an accurate method by which early diagnosis could be obtained in these diseases is highly desirable.

A substantial amount of research has been devoted to isolating antigens which may be useful in the selective detection of ovarian carcinomas. For example, Knauf and Urback (*Am. J. Obstet. Gynecol.* 138: 1222, 1980; *Cancer Res.* 41: 1351, 1981) have described an antigen named OCA which is significantly elevated in the plasma of 76% of patients with ovarian cancer; unfortunately, the antigen also occurs at high levels in about 10% of patients with benign gynecologic disorders, pregnant females and disease free controls, thus potentially rendering a positive test result unreliable. Similarly, Smith and Ol (*Obstet. & Gynecol. Surv.* 39: 346, 1984) report an ovarian cancer associated antigen, but this antigen has not yet been evaluated as to its specificity and suitability in diagnosis or monitoring of afflicted patients.

A recent discovery by Bast, et al. (*N. Engl. J. Med.* 309: 883 (1983) of a serous cystadinocarcinoma ovarian antigen, known as CA125, has proven to be of significant value in monitoring patients with ovarian cancer. This antigen was isolated by using a monoclonal antibody, OC125, raised by stimulation of mice with ovarian cancer cell line OVCA 433. It has been shown to recognize cell surface antigens of the OVCA 433 cell as well as 13 of 14 other ovarian cancer cell lines and a melanoma cell line. The antigen is a high molecular weight (>200,000 daltons) glycoprotein which has been partially purified from tissue culture medium (Masuko, et al., *Cancer Res.* 44: 2813, 1984). With use of the aforementioned monoclonal antibody, sera of several patients with various types of cancer was tested for the presence of CA125. Results showed that 83% of patients with ovarian cancer had elevated levels (>35 units/ml), whereas only 1% of 888 normal patients sera showed titers above this level. Although data indicate a certain level of non-ovarian specificity of the CA125 antigen, the observation of rising and falling levels of antigen with progression and regression of the disease in patients with ovarian cancer show utility of the antigen in monitoring the progress of the disease in already diagnosed patients. The use of CA125 for diagnostic purposes is further complicated by the fact it appears to be, to some extent, a normal product of development. Significant quantities have been found in amniotic fluid during gestation (O'Brien, et al., *Soc. Gyn Invest. Abstract*, p. 54, March, 1985. It has also been found to increase in connection with benign disease conditions such as endometriosis or pelvic inflammatory diseases. The existence of even small amounts of CA125 in normal tissue provides a significant chance of cross reactivity of the CA125-specific antibodies with non-tumor tissues as well as with cancerous tissues. Therefore, again, although there is substantial promise in the CA125 antigen as a potential marker for ovarian cancer, there has not yet been determined a method by which interference from non-ovarian tumor and normal tissue levels of CA125 can be eliminated. Further, the known monoclonal antibody OC125 appears to react with both the normal and tumor antigen. Therefore, there still does not exist a truly ovarian tumor specific immunoassay which can reliably be used to detect and monitor the ovarian carcinomas without the possibility of cross-reaction with normal tissue. It has now been unexpectedly discovered that the antigen CA125 contains a heretofore undiscovered subunit which appears to be specific to ovarian tumor-associated CA125. Normal tissue tested has failed to show the presence of this fraction of the CA125 molecule. Thus, the discovery of this unique subunit now presents a means by which the testing procedure utilizing CA125 as a marker for ovarian cancer can be refined to reduce or eliminate cross reaction with non-ovarian tumor associated CA125 antigen.

BRIEF DESCRIPTION OF THE INVENTION

The present invention relates to a subunit of CA125 antigen having a molecular weight of about 40,000 daltons, said subunit being found only in tumor associated CA125 antigen.

The invention also relates to a monoclonal antibody having specificity for the 40,000 daltons subunit of tumor-associated CA125.

The invention further relates to a method of detection or monitoring of ovarian cancer which comprises contacting serum of an individual suspected of having ovarian cancer with an antibody having specificity for the 40,000 dalton subunit of tumor-associated CA125.

DETAILED DESCRIPTION OF THE INVENTION

The discovery of a unique tumor-associated CA125 subunit has now provided a means by which sera of tumor-afflicted patients may be readily distinguished from sera of normal patients or those with benign gynecologic disorders. The novel subunit, which is readily isolatable from CA125 antigen, can then be used to prepare monoclonal antibodies which, when used in an immunoassay, will be capable of differentiating normal from tumor-associated sera by its specificity for the tumor-associated subunit.

CA125, the source of the relevant subunit, may be isolated from serum of patients known to have ovarian tumors. Although the antigen may be isolated by any of the methods known in the art for glycoprotein isolation, the most reliable method by which this may be achieved is by isolation using the CA125 antibody (available as a kit from Centocor Corp.), whereby the CA125 antigen is isolated by exposure to the bead bound monoclonal antibody. Alternatively, the CA125 antigen may be purified by molecular filtration. The 40KD subunit may then be isolated by electrophoresis of the CA125 antigen, followed by excision and elution of the 40KD band.

The subunit thus purified is then utilized in antibody production. Both polyclonal and monoclonal antibodies are obtainable by immunization with the present subunit, and either type is utilizable for the present immunoassays. The methods of obtaining both types of sera are well known in the art. Polyclonal sera are less preferred but are relatively easily prepared by injection of a suitable laboratory animal with an effective amount of the purified antigenic subunit, collecting serum from the animal, and isolating subunit-specific sera by any of the known immunoadsorbent techniques. Although antibodies produced by this method are utilizable in virtually any type of immunoassay, they are generally less favored because of the potential heterogeneity of the product.

The use of monoclonal antibodies in the present immunoassay is particularly preferred because of the ability to produce them in large quantities and the homogeneity of the product. The preparation of hybridoma cell lines for monoclonal antibody production derived by fusing an immortal cell line and lymphocytes sensitized against the immunogenic preparation can be done by techniques which are well known to those who are skilled in the art. (See, for example, Douillard, J. Y. and Hoffman, T., "Basic Facts About Hybridomas," in" Compendium of Immunology Vol. II, L. Schwartz (Ed.) (1981); Kohler, G. and Milstein, C., Nature 256, 495–497 (1975); European Journal of Immunology, Vol. 6, pp. 511–519 (1976), Koprowski, et al., U.S. Pat. No. 4,172,124, Koprowski, et al., U.S. Pat. No. 4,196,265 and Wands, U.S. Pat. No. 4,271,145, the teachings of which are herein incorporated by reference.)

Unlike preparation of polyclonal sera, the choice of animal is dependent on the availability of appropriate immortal lines capable of fusing with lymphocytes thereof. Mouse and rat have been the animals of choice in hybridoma technology and are preferably used. Humans can also be utilized as sources for sensitized lymphocytes if appropriate immortalized human (or nonhuman) cell lines are available. For the purpose of the present invention, the animal of choice may be injected with about 10 μg of the purified subunit. Usually the injecting material is emulsified in Freund's complete adjuvant. Boosting injections may also be required. The detection of antibody production can be carried out by testing the antisera with appropriately labeled antigen. Lymphocytes can be obtained by removing the spleen or lymph nodes of sensitized animals in a sterile fashion and carrying out fusion. Alternately, lymphocytes can be stimulated or immunized *in vitro*, as described, for example, in C. Reading *J. Immunol. Meth.* 53: 261–291, 1982.

A number of cell lines suitable for fusion have been developed, and the choice of any particular line for hybridization protocols is directed by any one of a number of criteria such as speed, uniformity of growth characteristics, deficiency of its metabolism for a component of the growth medium, and potential for good fusion frequency.

Intraspecies hybrids, particularly between like strains, work better than interspecies fusions. Several cell lines are available, including mutants selected for the loss of ability to secrete myeloma immunoglobulin. Included among these are the following mouse myeloma lines: $MPC_{11}$-X45-6TG, P3-NS1-1-Ag4-1, P3-X63-Ag8, or mutants thereof such as X63-Ag8.653, SP2-0-Ag14 (all BALB/C derived), Y3-'Agl.2.3 (rat), and U266 (human).

Cell fusion can be induced either by virus, such as Epstein-Barr or Sendai virus, or polyethylene glycol. Polyethylene glycol (PEG) is the most efficacious agent for the fusion of mammalian somatic cells. PEG itself may be toxic for cells, and various concentrations should be tested for effects on viability before attempting fusion. The molecular weight range of PEG may be varied from 1,000 to 6,000. It gives best results when diluted to about 50% w/w in saline or serum-free medium. Exposure to PEG at 37° C. for about 30 seconds is preferred in the present case, utilizing murine cells. Extremes of temperature should be avoided, and preincubation of each component of the fusion system at 37° C. prior to fusion gives optimum results. The ratio between lymphocytes and malignant cells should be optimized to avoid cell fusion among spleen cells. Myeloma-lymphocyte ratios ranging from 1:1 to 1:10 give good results.

The successfully fused cells can be separated from the myeloma line by any technique available to the art. The most common and preferred method is to choose a malignant line which is Hypoxanthine Guanine Phosphoribosyl Transferase (HGPRT) deficient, which will not grow in an aminopterin-containing medium used to allow only growth of hybrids is generally composed of hypoxanthine $1 \times 10^{-4}$, aminopterin $1 \times 10^5 M$, and thymidine $3 \times 10^{-5} M$, commonly known as the HAT medium. The fusion mixture can be grown in the HAT-containing culture medium immediately after the fusion or 24 hours later. The feeding schedules usually entail maintenance in HAT medium for two weeks and then feeding with either regular culture medium or hypoxanthine, thymidine-containing medium.

The growing colonies are then tested for the presence of antibodies that recognize the antigenic preparation. Detection of hybridoma antibodies can be performed using an assay where the antigen is bound to a solid support and allowed to react to hybridoma supernatants containing putative antibodies. The presence of antibodies may be detected by "sandwich" techniques using a variety of indicators. Most of the common methods are sufficiently sensitive for use in the range of antibody concentrations secreted during hybrid growth.

Cloning of hybrids can be carried out after 21–23 days of cell growth in selected medium. Cloning can be performed by cell limiting dilution in fluid phase or by directly selecting single cells growing in semi-solid agarose. For limiting dilution, cell suspensions are diluted serially to yield a statistical probability of having only one cell per well. For the agarose technique, hybrids are seeded in a semisolid upper layer, over a lower layer containing feeder cells. The colonies from the upper layer may be picked up and eventually transferred to wells.

Antibody-secreting hybrids can be grown in various tissue culture flasks, yielding supernatants with variable concentrations of antibodies. In order to obtain higher concentrations, hybrids may be transferred into animals to obtain inflammatory ascites. Antibody-containing ascites can be harvested 8–12 days after intraperitoneal injection. The ascites contain a higher concentration of antibodies but include both monoclonals and immunoglobulins from the inflammatory ascites. Antibody purification may then be achieved by, for example, affinity chromatography.

The presence of the CA125 40KD subunit antigen in a patient's serum can be detected utilizing these antibodies, either monoclonal or polyclonal, in virtually any type of immunoassay. This, of course, includes both single-site and two-site, or "sandwich," assays of the non-competitive types, as well as in traditional competitive binding assays. Sandwich assays are among the most useful and commonly used assays and are favored for use in the present invention. A number of variations of the sandwich assay technique exist, and all are intended to be encompassed by the present invention. Briefly, in a typical forward assay, an unlabeled antibody is immobilized on a solid substrate and the sample to be tested brought into contact with the bound molecule. After a suitable period of incubation, for a period of time sufficient to allow formation of an antibody-antigen binary complex, a second antibody, labeled with a reporter molecule capable of producing a detectable signal is then added and incubated, allowing time sufficient for the formation of a ternary complex of antibody-labeled antibody. Any unreacted material is washed away, and the presence of the antigen is determined by observation of a signal produced by the reporter molecule. The results may either be qualitative, by simple observation of the visible signal, or may be quantitated by comparing with a control sample containing known amounts of hapten. Variations on the forward assay include a simultaneous assay, in which both sample and labeled antibody are added simultaneously to the bound antibody, or a reverse assay in which the labeled antibody and sample to be tested are first combined, incubated and then added to the unlabeled surface bound antibody. These techniques are well known to those skilled in the art, and then possibly of minor variations will be readily apparent. As used herein, "sandwich assay" is intended to encompass all variations on the basic two-site technique.

The antigen may also be detected by a competitive binding assay in which a limiting amount of antibody specific for the molecule of interest (either an antigen or hapten) is combined with specified volumes of solutions containing an unknown amount of the molecule to be detected and a solution containing a detectably labeled known amount of the molecule to be detected or an analogue thereof. Labeled and unlabeled molecules then compete for the available binding sites on the antibody. Phase separation of the free and antibody-bound molecules allows measurement of the amount of label present in each phase, thus indicating the amount of antigen or hapten in the sample being tested. A number of variations in these general competitive binding assays currently exist.

In any of the known immunoassays, for practical purposes, one of the antibodies will be typically bound to a solid phase and a second molecule, either the second antibody in a sandwich assay, or, in a competitive assay, the known amount of antigen, will bear a detectable label or reporter molecule in order to allow visual detection of an antibody-antigen reaction. When two antibodies are employed, as in the sandwich assay, it is only necessary that one of the antibodies be specific for the 40KD subunit, while the other may be specific for the subunit or for the CA125 antigen. The following description will relate to a discussion of a typical forward sandwich assay; however, the general techniques are to be understood as being applicable to any of the contemplated immunoassays.

In the typical forward sandwich assay, a first antibody having specificity for the subunit molecule is either covalently or passively bound to a solid surface. The solid surface is typically glass or a polymer, the most commonly used polymers being cellulose, polyacrylamide, nylon, polystyrene, polyvinyl chloride or polypropylene. The solid supports may be in the form of tubes, beads, discs or microplates, or any other surface suitable for conducting an immunoassay. The binding processes are well-known in the art and generally consist of cross-linking covalently binding or physically adsorbing the molecule to the insoluble carrier. Following binding, the polymer-antibody complex is washed in preparation for the test sample. An aliquot of the sample to be tested is then added to the solid phase complex and incubated at 25° C. for a period of time sufficient to allow binding of any subunit present to the antibody. The incubation period will vary but will generally be in the range of about 2–40 minutes. Following the incubation period, the antibody subunit solid phase is washed and dried and incubated with a second antibody specific for a portion of the hapten. The second antibody is linked to a reporter molecular which is used to indicate the binding of the second antibody to the hapten. By "reporter molecule," as used in the present specification and claims, is meant a molecule which, by its chemical nature, provides an analytically indicatable signal which allows the detection of antigen-bound antibody. Detection may be either qualitative or quantitative. The most commonly used reporter molecules in this type of assay are either enzymes, fluorophores or radionuclide containing molecules. In the case of an enzyme immunoassay, an enzyme is conjugated to the second antibody, generally by means of glutaraldehyde or periodate. As will be readily recognized, however, a wide variety of different conjugation techniques exist, which are readily available to the skilled artisan. Commonly used enzymes include horseradish peroxidase, glucose oxidase, $\beta$-galactosidase and alkaline phosphatase, among others. The substrates to be used with the specific enzymes are generally chosen for the production, upon hydrolysis by the corresponding enzyme, of a detectable color change. For example, p-nitrophenyl phosphate is suitable for use with alkaline phosphatase conjugates; for peroxidase conjugates, 1,2-phenylenediamine, 5-aminosalicyclic acid, or tolidine are commonly used. It is also possible to employ fluorogenic substrates, which yield a fluorescent product rather than the chromogenic substrates noted above. In all cases, the enzyme-labeled antibody is added to the first antibody hapten complex, allowed to bind, and then to the first antibody hapten complex, allowed to bind, and then the excess reagent is washed away. A solution containing the appropriate substrate is then added to the ternary complex of antibody-antigen-antibody. The substrate will react with the enzyme linked to the second antibody, giving a qualitative visual signal, which may be further quantitated, usually spectrophotometrically, to give an indication of the amount of hapten which was present in the sample.

Alternately, fluorescent compounds, such as fluorescein and rhodamine, may be chemically coupled to antibodies without altering their binding capacity. When activated by illumination with light of a particular wavelength, the fluorochrome-labeled antibody absorbs the light energy, inducing a state of excitability in the molecule, followed by emission of the light at a characteristic longer wavelength. The emission appears as a characteristic color visually detectable with a light microscope. As in the EIA, the fluorescent labeled antibody is allowed to bind to the first antibody-hapten complex. After washing off the unbound reagent, the remaining ternary complex is then exposed to light of the appropriate wavelength, the fluorescence observed indicates the presence of the hapten of interest. Immunofluorescence and EIA techniques are both very well established in the art and are particularly preferred for the present method. However, other reporter molecules, such as radioisotope, chemiluminescent or bioluminescent molecules, may also be employed. It will be readily apparent to the skilled technician how to vary the procedure to suit the required purpose.

In a further embodiment, the present invention also relates to a kit for the detection of ovarian cancer, the kit being compartmentalized to receive a first container containing an antibody having specificity for the 40 kilodalton subunit and a second container containing a second antibody having specificity for the 40 kilodalton subunit of CA125, or for CA125 itself, one of the antibodies being labeled with a reporter molecule capable of giving a detectable signal and another of the antibodies being immobilized on a solid surface.

The present methods and kit are applicable to the detection and monitoring of virtually any type of ovarian cancer. It is particularly well adapted to the detection by cystadenocarcinomas, which comprise about 75% of all ovarian cancers.

The practice of the present invention will be more fully understood by reference to the following examples.

EXAMPLE 1

Isolation and Purification of CA125 Tumor Subunit

CA125 tumor antigen is purified from ascites fluid collected from ovarian tumor patients. Ascites fluid is centrifuged at 10,000×g prior to storage at −20° C. in aliquots of 10 ml. Aliquots (10 ml) are removed for CA125 purification and applied to a 100 cm×5 cm column filled to half its volume with HW 55 fractogel (EM reagents) and the other half filled with HW 65 fractogel. HW55 and HW65 are molecular filtration beads designed to separate molecules of high molecular weight. The combination of HW55 and HW65 first separates molecules of 700,000 daltons or higher by exclusion from HW55. These molecules are further size fractionated on HW65 which segregates molecules up to $5 \times 10^6$ daltons. Ascites fluid is processed over this column using 0.15M NaCL in 20 mM Bis-Tris propane buffer pH 7.2 and 0.1% sodium azide. Nine milliliter fractions are collected, and CA125 activity is monitored using the available commercial assay kit. CA125 elutes over a broad range of molecular size from approximately $1 \times 10^6$ daltons to $4 \times 10^6$ daltons. Fractions containing activity are pooled and dehydrated in dialysis bags using flake polyethene glycol (Bio-rad Aqueside II). The dehydrated material containing the CA125 activity is dehydrated in deionized water and extensively dialyzed ($\times 3$) against distilled × deionized water. The cloudy suspension is clarified using centrifugation at 15,000 RPM for 20 minutes to pellet the insoluble material. No CA125 activity is lost to the pellet by this procedure. Further purification of CA125 is accomplished by filtration of the supernatant over a 0.22 $\mu m$ sterile filter (Amicon Inc.). The filtrate may then be aliquoted into 1 ml eppinderf/microtubes and lyophilized to dryness using a speed vac centrifuge lyophilization procedure.

Dried samples are resuspended as needed in SDS sample buffer (60 mM Tris pH 6.8 5% mercaptoethanol, 3% sodium dodecyl sulfate, 10% glycerol) and electrophoreses over 12% polyacrylamide gels according to the method of Laemmli (Laemmli U.K. *Nature* 227: 680, 1970). Commassie Blue staining of gels after electrophoresis indicates the presence of the 40K dalton protein, a 50K dalton protein and a 92K dalton protein. The peptide bands can be excised from the gel using a standard scalpel after identification of the band location with Commassie Blue. The 40 KD band is then electroluted from the gel using a Biorad electroeluter in electroelution buffer (25 mM Tris Base 192 MM glycine 0.1% SDS pH 8.3) for 3 hours at 150 volts. The sample is collected approximately 1 ml and dialyzed against 2M NaCL 4 mM Tris pH 7.0 for $3 \times$ changes followed by dialysis against deionized water overnight. The sample is dried using a speed vac and stored at $-70°$ C. Confirmation of purity of individual subunits including the 40KD subunit is confirmed by reelectrophoresis.

Iodination of either purified CA125 antigen or bead selected (antibody selected) antigen followed by SDS polyacrylamide gels confirms the presence of the 40KD subunit of the CA125 tumor derived antigen.

EXAMPLE 2

Polyclonal Antibody Preparation

Rabbits are immunized by intradermal injection with 50 $\mu l$ of Freund's complete adjuvant containing 20 $\mu g/ml$ of purified CA125 40KD subunit antigen in 10 locations along the back. The rabbits are first shaved on both sides of the back for easy intradermal injection. The antigen-adjuvant mixture is prepared by mixing in two connected 1 ml glass typhlon syringes and administered in 100 $\mu l$ doses per location. Forty days after injection rabbits are boosted by direct intraveneous injection of 10 $\mu g/100$ $\mu l$ PBS of antigen. Seven to ten days later, rabbits are bled via the ear vein and sera tested for presence of anti-CA125 40KD antibodies. Screening and titration of rabbit antisera is accomplished using $^{125}I$ labelled 40KD subunit in the presence of goat anti-rabbit coated latex beads.

EXAMPLE 3

Monoclonal Antibody Production

Monoclonal antibodies are prepared in accordance with the techniques developed by Kohler and Milstein (*Eur. J. Immunol.* 6: 511–519, 1976). Mice are immunized with CA125 40KD subunit intraperitoneally with 10 $\mu g$ of subunit in 100 $\mu l$ of Freund's complete adjuvant. Two weeks after the initial injection, the mice are boosted with 10 $\mu g$ of antigen in 100 $\mu l$ of alum (10 mg/ml) by intraperitoneal injection of 10 $\mu g$ of antigen in phosphate buffered saline (PBS).

Five days after the last injection and after confirmation of the presence of antibody in mouse sera, the mice are sacrificed and their spleens removed. Spleen cells are obtained by gentle disruption of the spleen in a 7 ml Dounce homogenizer in 3.5–4 ml PBS. The cells are then pelleted at 1200 rpm in a PR6 centrifuge for 6 minutes at room temperature. The supernatant is removed into a suction flask, and the cells are resuspended in 15 ml 0.83% $NH_4Cl$. This suspension is incubated at room temperature for 5 minutes then underlain with 10 ml fetal calf serum at 37° C. The cells are again pelleted by centrifugation for 8 minutes, at 1200 rpm at room temperature, then the supernatant is withdrawn into a suction flask and cells resuspended in 20 ml PBS.

The following solutions are prepared for use in the subsequent cell fusion: Hypoxanthine (H), 680 mg/100 ml $H_2O$; add 2–4 drops conc. $H_2SO_4$; heat to dissolve Aminopterin (A), 46.4 mg/100 ml $H_2O$; add 2 drops 1.0N NaOH to dissolve Thymidine (T), 775 mg/100 ml $H_2O$; add 45 mg glycine PEG-DME--melt PEG @ 42° C., then add 1 ml DME (@ 37° C.); adjust pH with 1.0N NaOH to 7.6 DMEM--to 500 ml DME add 37.5 ml a-horse serum; 37.5 ml FCS, 10.0 ml L-glutamine, and 0.5 ml garamycin 2× HAT-DME--to 200 ml DME add 25.0 ml a-horse serum, 25.0 ml FCS, 4.0 ml L-glutamine, 0.2 ml garamycin, 0.8 ml H, and 0.8 ml A, and 0.8 ml T (2× HT-DME omits A) Cloning Agar--350 mg unwashed Difco agar in 25 ml $H_2O$, autoclaved Cloning Medium--to 25 ml 2× DME, add 35 ml filtered, condition DMEM, 7 ml a- HS, 7 ml FCS, 1 ml L-glutamine, 0.1 ml garamycin Two 30 ml flasks of Sp2/0 cells are added to centrifuge tubes and spun down at 1200 rpm for 8 minutes at room temperature. The spleen cells are resuspended in 20 ml PBS. From each suspension, 0.01 ml is removed and added to 0.1 ml 0.4% trypan blue and 0.3 ml PBS and the cells counted. The volume of each suspension is adjusted so as to obtain a spleen cell to Sp2/0 cell ratio of 10:1, and the suspensions are then mixed. The mixture is pelleted at 1200 rpm for 8 minutes at room temperature and all but about 0.1 ml of supernatant removed. The cells are then resuspended in the remaining liquid and then added to 1.3 ml of a 1:1 PEG-DME solution, pH 7.6. Every minute the volume of the solution is doubled with DME until the final volume is 25 ml.

The cells are again pelleted, the supernatant decanted, and the cells resuspended in enough 50% 2× HAT-DME/50% conditioned DMEM (the supernatant retained from the Sp2/0 cells above) to yield a final concentration of about $3.5 \times 10^6$ spleen cells. The cells are distributed into a 96-well flat-bottom microtiter plate (TC-96; Flow Laboratories), at 0.1 ml/well. The plate is incubated at 37° C. in humidified air/CO$_2$ until visible colonies appear, usually about 10–12 days. The content of the well is transferred to 0.5 ml of HT-DME/conditioned DMEM in a TC-24 plate (Flow Laboratories). When healthy cell growth appears (about 2–5 days), about 0.35 ml medium is removed and tested for antibody production by enzyme-linked immunosorbent assay (ELISA), Hemagglutinin inhibition assay, or neuraminidase inhibition assay. When those cells producing the antibodies of interest are growing well, one drop from each culture is transferred into 1.0 ml DMEM in a TC-24.

To clone the hybrid cells, 25 ml of melted agar and 76 ml of cloning medium is combined, and 5 ml is pipetted into 60 mm petri dishes and left to solidify. Cells from DMEM cultures are diluted in 50% DMEM/50% conditioned DMEM, $10^{-1}$ or $10^2$ depending on cell growth. Into sterile tubes is placed 0.1 ml of each of the two dilutions, and to each is added 0.9 ml of cloning medium/agar mixture. This is mixed well and poured over the surface of the agar underlay. After solidification the plates are incubated at 37° C. incubator until colonies are visible with the naked eye, typically about 7–10 days. Colonies are then picked and transferred to 0.1 ml of DMEM/conditioned DMEM in a TC-99 plate and incubated at 37° C. in a CO$_2$ incubator. After the culture is acidic (usually 1–4 days), transfer is made to 0.05 ml DMEM in TC-24 plate. When the growth is 50% connfluent, the medium is removed and tested for antibody production as previously. Those clones producing the 40KD subunit specific antibody are moved into 5 ml DMEM in 25 cm$^2$ flasks. Cloned cells are then frozen or injected into mice for ascites production.

EXAMPLE 4

Sandwich Assay for 40KD Subunit Antigen

For detection of the presence of tumor specific antigen in serum, approximately 100 μl of a monoclonal antibody prepared as in Example 3 is immobilized on latex beads and is contacted with about 100 μl of the serum sample to be tested. The antibody and serum are allowed to react for a period of about ten minutes and then rinsed with a solution of PBS. To the latex beads is then added about 100 μl of CA125 specific antibody conjugated to horseradish peroxidase. The labelled antibody bead mixture is incubated for a period of about ten minutes. At this time, an enzyme substrate, hydrogen peroxide and aminoantipyrine, are contacted with the beads, and this mixture is incubated for a period of about 5–10 minutes, at which time the development of color in the sample is an indication of a positive reaction and the presence of the tumor-specific 40KD antigen.

The foregoing procedure is also conducted with two monoclonal antibodies specific for the 40KD antigen, or a monoclonal or a polyclonal, or two polyclonals specific for the 40KD antigen. It is also possible to conduct the assay with only one antibody specific to the 40KD subunit, and a second one which is specific for the CA125 antigen.

What is claimed is:

1. An isolated subunit of serous cystadinocarcinoma ovarian tumor associated CA125 antigen having a molecular weight of about 40 kDa.

2. An antibody having specificity for a 40 kilodalton molecular weight subunit of serous cystadinocarcinoma ovarian tumor associated antigen CA125.

3. The antibody of claim 2 which is a monoclonal antibody.

4. A method of detection of ovarian cancer which comprises the steps of contacting the serum of an individual suspected of having the cancer with at least one antibody having specificity for a 40 kilodalton subunit of serous cystadinocarcinoma ovarian tumor associated antigen CA125 and detecting a subunit-antibody reaction.

5. The method of claim 4 which comprises the steps of:
  (a) contacting serum of a patient suspected of having ovarian cancer with a first antibody having specificity for either the 40 kilodalton molecur weight subunit of the CA125 antigen or for the CA125 antigen, the first antibody being bound to a solid surface, and allowing time sufficient for formation of a binary complex;
  (b) adding to the binary complex a second antibody having specificity either for the subunit or for the CA125 antigen, the second antibody being labeled with a reporter molecule capable of giving a detectable signal, and allowing time sufficient for formation of a ternary complex, at least one of said antibodies having specificity for the 40 kilodalton subunit;
  (c) detecting the presence of the ternary complex by observing the detectable signal of the reporter molecule.

6. A kit for the diagnosis and monitoring of ovarian cancer, the kit containing: (a) a first container containing an antibody having specificity for a 40 kilodalton molecular weight subunit of serous cystadinocarcinoma ovarian tumor associated CA125 antigen; (b) a second container containing a second antibody having specificity for serous cystadinocarcinoma ovarian tumor associated CA125 antigen or the 40 kilodalton subunit;
one of said antibodies being immobilized on a solid surface and another of said antibodies being labelled with a reporter molecule capable of giving a detectable signal.

7. The kit of claim 6 wherein the reporter molecule is a radioisotope, an enzyme, a fluorescent molecule, a chemiluminescent molecule or a bioluminescent molecule.

8. The kit of claim 6 wherein the reporter molecule is an enzyme.

9. The kit of claim 8 wherein the kit further comprises:
  (c) a third container containing a substrate for the enzyme.

* * * * *

UNITED STATES PATENT AND TRADEMARK OFFICE
CERTIFICATE OF CORRECTION

PATENT NO.   :  4,921,790
DATED        :  May 1, 1990
INVENTOR(S)  :  Timothy J. O'Brien It is certified that error appears in the above-identified patent and that said Letters Patent is hereby corrected as shown below:

Column 1, line 7: "Institute" should read as --Institutes--

Column 2, line 42: after "effectively" delete --been--

Column 4, line 59: "in"" should read as --in--

Column 10, line 46: "a-" should read as --a- & --

Column 10, line 49: "a-horse serum" should read as --a- & horse serum--

Column 10, line 54: "a-HS" should read as --a- & horse serum--

Column 12, line 7, Claim 1: "CA125 antigen" should read as --antigen CA125--

Column 12, line 26, Claim 5: "molecur" should read as --molecular--

Signed and Sealed this

Tenth Day of September, 1991

*Attest:*

HARRY F. MANBECK, JR.

*Attesting Officer*   *Commissioner of Patents and Trademarks*